Figure 1:
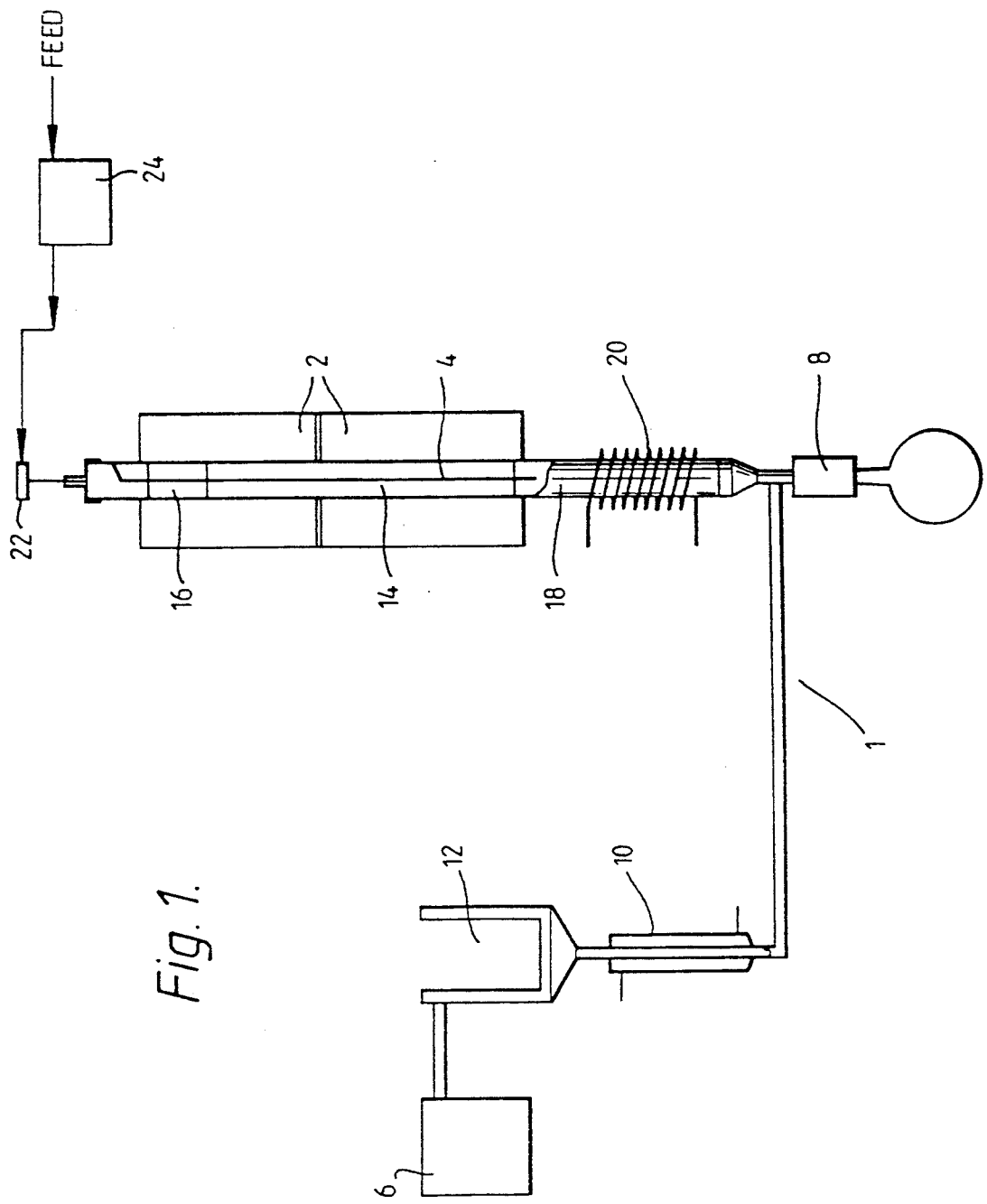

United States Patent [19]

Newman

[11] Patent Number: 5,313,008
[45] Date of Patent: May 17, 1994

[54] 8-HYDROXYCYMENE PREPARATION BY DEHYDROGENATION

[75] Inventor: Christopher P. Newman, Canterbury, Great Britain

[73] Assignee: Unilever Patent Holdings B.V., Vlaardingen, Netherlands

[21] Appl. No.: 42,776

[22] Filed: Apr. 6, 1993

[30] Foreign Application Priority Data

Apr. 6, 1992 [EP]  European Pat. Off. ........ 92303006.8

[51] Int. Cl.$^5$ ........................ C07C 29/00; C07C 27/00
[52] U.S. Cl. ...................... 568/814; 568/715; 568/726
[58] Field of Search ................... 568/814, 826

[56] References Cited

U.S. PATENT DOCUMENTS

| | | | |
|---|---|---|---|
| 2,361,532 | 10/1944 | Cox | 568/814 |
| 2,366,409 | 1/1945 | Johnston | 568/814 |

FOREIGN PATENT DOCUMENTS

| | | | |
|---|---|---|---|
| 512236 | 4/1955 | Canada | 568/814 |
| 5933 | 5/1972 | Japan | 568/814 |
| 699062 | 10/1953 | United Kingdom | 568/814 |

*Primary Examiner*—Werren B. Lone
*Attorney, Agent, or Firm*—Cushman, Darby & Cushman

[57] ABSTRACT

The invention relates to a process for the conversion of 8-hydroxymenthenes into 8-hydroxycymenes by treating the 8-hydroxymenthenes in the vapour phase with an alkaline dehydrogenation catalyst, e.g. palladium on an alkaline support. The process is carried out above 145° C. The hydroxymenthene vapour is preferably passed through the catalyst system at a pressure below 8 kPa and/or with the aid of an inert gas or vapour. Oxygen may be present as a hydrogen acceptor. The process is particularly suitable for converting 8-hydroxy-p-menth-1-ene into 8-hydroxy-p-cymene. The reaction products are of value as intermediates in the preparation of musk fragrance chemicals.

17 Claims, 1 Drawing Sheet

8-HYDROXYCYMENE PREPARATION BY DEHYDROGENATION

The present invention relates to the production of intermediates suitable for the preparation of fragrances. In particular, this invention relates to improvements in the production of 8-hydroxycymenes by vapour phase dehydrogenation.

Important substances in the preparation of perfumes are fragrances of the indane and tetralin musk type such as 7-acetyl-1,1,3,4,4,6-hexamethyltetralin. These substances have excellent odour and fixative properties. They are stable to alkali and light, soluble in most solvents, substantially colourless and persistent and are also relatively cheap. They are commonly prepared by acetylation of the corresponding methyl-substituted indane or tetralin in a Friedel-Crafts reaction. Several routes have been proposed for the preparation of these latter substances involving the formation of an alicyclic attachment to substituted cymenes which in turn may be obtained from 8-hydroxycymene.

It is known from U.S. Pat. No. 2,366,409 (Hercules) that 8-hydroxymenthene can be converted in the liquid phase to a mixture of 8-hydroxycymene and 8-hydroxymenthane by means of a disproportionation reaction. This reaction appears to be a combination of hydrogenation and dehydrogenation i.e. is a transfer hydrogenation. For every molecule of 8-hydroxymenthene which is dehydrogenated, enough hydrogen is produced to hydrogenate two molecules of 8-hydroxymenthene to 8-hydroxymenthane. A significant improvement on this route has been disclosed in EP-A-416683, involving the use of an added hydrogen acceptor, thus enabling substantial improvements in the yield of 8-hydroxycymene. A different process is disclosed in EP-A-417825, involving the vapour phase dehydrogenation of 8-hydroxymenthenes, again leading to a significant improvement in the yield of 8-hydroxycymenes and a concomitant decrease in unwanted 8-hydroxymenthanes. All these reactions are carried out in the presence of dehydrogenation catalysts, preferably a Group VIII metal in activated form.

In both European patent applications mentioned above reaction conditions are carefully controlled in order to prevent dehydration from taking place, leading to cymene and thus diminishing the yield of the desired 8-hydroxycymenes. Thus, the importance of maintaining non-acid conditions during the dehydrogenation is stressed in both applications. In the examples in EP-A-416683 the reaction is carried out in the liquid phase in the presence of alkali or alkaline earth carbonates. In the examples of EP-A-417825 before the gas phase reaction is started the catalyst is washed acid-free by soaking and leaving in aqueous alkali for 2 hours, followed by washing with water until neutral. In the liquid phase, where the reaction is carried out in the presence of base, as well as in the gas phase, where the catalyst is neutral, the importance of tight temperature control to prevent dehydration is stressed. Thus, in both European patents a maximum temperature of 150° C. is mentioned. Preferably the reaction is carried out below 145° C. with an optimum around 135°–142° C.

In contrast, it has now been found that the vapour phase dehydrogenation can successfully be carried out at temperatures substantially above 145° C. by using an alkaline dehydrogenation catalyst. Thereby the yield of 8-hydroxycymenes is increased while at the same time maintaining the amount of cymenes (dehydration products) at an acceptable level. Accordingly, the invention provides a process for the vapour phase catalytic conversion of 8-hydroxymenthenes to 8-hydroxycymenes which comprises treating an 8-hydroxymenthene with an alkaline dehydrogenation catalyst at a temperature above 145° C.

The starting material for the method in accordance with this invention may be any 8-hydroxymenthene. The carbon structure of the menthenes will be found in Bernthsen, Textbook of Organic Chemistry, Sudborough Revision, 1922 edition D. Van Nostrand Company, New York, N.Y., page 609 and page 613. The system of numbering the carbon atoms shown there will be utilized herein. It will be appreciated that the methyl group represented by carbon No. 7 may be para, ortho or meta with respect to the isopropyl group. 8-Hydroxy-menthadienes are included within the term 8-hydroxymenthene.

The hydroxymenthene may be in the form of a pure compound, or it may be in the form of a mixture, e.g. a distillation cut reasonably rich therein. For example, 8-hydroxy-p-menth-1-ene (alpha-terpineol) may be utilized in a fairly pure state, or it may be utilized in the form of ordinary commercial pine oil, which is usually a mixture of terpene alcohols. It will be understood that where the 8-hydroxymenthenes utilized have the para-menthene configuration, as is the case with 8-hydroxy-p-menth-1-ene, the derivatives will have the same para arrangement. Similarly, ortho- and meta-hydroxy-menthenes lead to ortho and meta products respectively.

Different methods are available and described in the prior art referred to above, to achieve the vapour phase, e.g. by raising the temperature of the 8-hydroxymenthene feedstock above its boiling point, which for alpha-terpineol is about 220° C. at atmospheric pressure. To carefully control the course and speed of the reaction it is preferably carried out under reduced pressure, particularly below 8 kPa, even more preferably from 0.1 to 5 kPa, and most preferably from 0.1 to 2 kPa. Alternatively, the vapour phase may be achieved by vaporizing the substrate with the aid of an inert carrier gas e.g. nitrogen, or vapour e.g. steam or mixtures thereof. The use of controlled low pressure or a carrier gas or vapour also serves to remove hydrogen gas produced during the conversion from the reaction system, thereby minimising the production of 8-hydroxymenthane.

The conversion is preferably carried out at a temperature below 300° C., preferably below 250° C., more preferably below 230° C. At the lower end of the temperature range, temperatures of 150° C. or above are preferred. The reaction system can be maintained at the desired temperature by any heat transfer system, for example hot oil or steam, or by direct electrical heating.

The catalyst is preferably a metal of Group VIII in activated form, particularly palladium, but metals such as platinum, ruthenium, rhodium, iridium or osmium may be used as well. They may be supported on conventional support media e.g. silicas, alumina or carbon, suitably at levels of from 0.1 to 10% by weight. A particularly suitable catalyst is 0.2% by weight palladium on an alumina support, available commercially e.g. as Engelhard PGCS2. The catalyst is suitably made alkaline with a base additive such as an alkali or alkaline earth metal hydroxide or carbonate or other suitable salt or a suitable ion exchange resin. A very convenient way of doing this is by pre-washing the catalyst with a base solution, which is thereafter drained from the catalyst.

The alkali value of the catalyst should be at least 0.1 mg KOH/g catalyst, preferably 1.0 mg or higher, typically 2.8 mg or higher.

Air or oxygen may be introduced into the system; oxygen acts as a hydrogen acceptor, removing the free hydrogen from the system as water vapour. Other suitable hydrogen acceptors may be used. Formation of water is highly exothermic and care is needed in the control of the reaction temperature. Therefore, when air or oxygen is introduced into the system it is desirable to operate the conversion at a pressure of less than 5 kPa at which pressure combinations of oxygen and hydrogen present a less hazardous mixture. Alternatively, mixtures of air or oxygen with an inert gas or vapour as mentioned above may be used. Thus, not only is the substrate vaporized but also the transfer of hydrogen to the hydrogen acceptor is controlled.

When the reaction is carried out batch-wise the catalyst can be recovered and reused. For batch-wise as well as continuous operation the lifetime of the catalyst is influenced by the reaction temperature and the possible presence of catalyst-poisoning components in the feedstock. In particular sulphur and halogen compounds and certain hydrocarbons, all of which may be present in minute quantities in some feedstocks, have a negative influence on catalyst life-time. It can therefore be beneficial to subject feedstocks which contain such contaminants to a purifying pretreatment, which may include one or more of: heating or washing with base, oxidation (e.g. with hydrogen peroxide), reduction, treatment with activated carbon, sacrificial metal catalyst treatment or treatment with commercial desulphurisation or dehalogenation materials such as Puraspec 7186 or Puraspec 7040 (marketed by Katalco). Another beneficial treatment may be the use of catalyst cleaning agents, e.g. water (see Beren Blyum A. S. et al, Kinet. Katal. 1985, 26(3), pp 626–631).

Accordingly, the invention also comprises 8-hydroxymenthene-rich feedstocks which have been treated to free them from catalyst-poisoning contaminants.

The 8-hydroxycymenes obtained by the process according to the invention may be separated from the reaction mixture according to the usual procedures described in the art and are thereafter excellently suitable from the preparation of indane and tetralin precursors for musk fragrances. The product mixture obtained from the reaction may also be used as such without further separation of the 8-hydroxycymenes therefrom.

The invention is further illustrated by the following Example.

EXAMPLE 1

Tubular stainless steel reactors (1) were used (see schematic diagram, FIG. 1), capable of operating under reduced pressure and equipped with heaters (2), central thermocouple well (4), and connected to a vacuum pump (6) via a fraction cutter (8), condenser (10) and cold trap (12). The stainless steel reactor, internal diameter 25 mm, is packed with 156 g of Engelhard PGCS2 catalyst (0.2% by weight Palladium on alumina spheres (eggshell)). On top of the catalyst bed (14) is a section (16) packed with glass helices to act as a flash heater. The catalyst bed length is 45 cm and the flash heater length is 10 cm. Beneath the catalyst bed is a section (18) packed with knitmesh with an exterior cooling coil (20) to act as a condenser. Prior to use the reactor containing the catalyst is filled with 0.2% by weight sodium hydroxide solution and left to stand for 3 hours. It is then washed twice with distilled water, which after draining from the reactor has a pH of 13. The damp catalyst is dried by warming to c.a. 150 C in a stream of inert gas (nitrogen). It loses any remaining water when the pressure is reduced stepwise to that required for the reaction conditions, which is c.a. 0.5 kPa.

The reactor used in this example comprised six reactor tubes operating parallel and driven by a common wiped film evaporator. Each tube had an internal diameter of 25 mm and was packed with washed catalyst as described above to a bed length of 45 cm. The reactor is equipped with an appropriately sized vacuum pump and condensing system. The reactor was charged with 967 g catalyst (dry weight prior to washing). After the pressure was lowered to 0.5 kPa the bed was reduced under a stream of hydrogen at 0.6 kPa for 1.5 hrs. The flow rate of the hydrogen was c.a. 0.1 g/min. Terpineol vapour[1] at 140°–160° C. was introduced to the reactor bed at a rate of 0.4 kg/hr and the hydrogen flow stopped. The temperature of the reactor was increased to 195°–200° C. and after equilibration of the system, 236.9 kg of terpineol were introduced to the reactor at 0.4 kg/hr for a period of 588 hrs[2]; 231.3 kg of condensed crude product were pumped from the receiver vessel and collected. The latter comprised 154.78 kg of p-cymen-8-ol, 49.40 kg of dihydroterpineol isomers, 11.98 kg of p-cymene and 10.2 kg of terpineol. The mass recovery was 98.2%.

Note 1: The terpineol feed comprised c.a. 78% of the α-isomer and 10% of the γ-isomer.

Note 2: There appeared to be no loss of catalyst activity at the end of this period.

I claim:

1. Process for the vapour phase catalytic conversion of an 8-hydroxymenthene to an 8-hydroxycymene which comprises treating an 8-hydroxymenthene with an alkaline dehydrogenation catalyst at a temperature above 145° C.

2. A process according to claim 1 wherein the 8-hydroxymenthene is 8-hydroxy-p-menth-I-ene.

3. A process as claimed in claim 1 wherein the dehydrogenation catalyst comprises a Group VIII metal.

4. A process as claimed in claim 3 wherein the dehydrogenation catalyst comprises palladium.

5. A process as claimed in claim 1 wherein the conversion is carried out at a temperature of 150° C. or above.

6. A process as claimed in claim 5 wherein the conversion is carried out at a temperature of from 150° to 250° C.

7. A process as claimed in claim 1 wherein the conversion is carried out at a pressure of less than 8 kPa.

8. A process as claimed in claim 7 wherein the conversion is carried out at a pressure of from 0.1 to 5.0 kPa.

9. A process as claimed in claim 1 wherein the 8-hydroxymenthene is introduced into the catalyst system by means of an inert gas or vapour.

10. A process as claimed in claim 9 wherein the inert vapour is steam.

11. A process as claimed in claim 1 wherein air or oxygen is added with the 8-hydroxymenthene to act as a hydrogen acceptor.

12. Use of the product mixture, obtained by vapour phase catalytic conversion of an 8-hydroxymenthene to an 8-hydroxycymene using an alkaline dehydrogenation catalyst at a temperature above 145° C., for the preparation of indane or tetralin precursors for musk fragrances.

13. 8-Hydroxymenthene-rich feedstock for vapor phase catalytic dehydrogenation, which has been treated to free it from catalyst-poisoning contaminants.

14. Feedstock according to claim 13 obtained by treating pine oil.

15. A process according to claim 1 wherein the alkaline dehydrogenation catalyst has an alkali value of at least 0.1 mg KOH/g catalyst.

16. A process according to claim 1 wherein 8-hydroxymethene-rich feedstock for said vapor phase catalytic dehydrogenation has been treated to free said feedstock from catalyst-poisoning contaminants.

17. A process according to claim 16 wherein said feedstock is obtained by treating pine oil.

* * * * *